United States Patent [19]

Steggles et al.

[11] Patent Number: 4,675,334

[45] Date of Patent: Jun. 23, 1987

[54] TETRAZOLYL COMPOUNDS AND THEIR USE AS ANTI ALLERGIC AGENTS

[75] Inventors: David J. Steggles, Bracknell; John P. Verge, Henley-on-Thames, both of England

[73] Assignee: Lilly Industries Limited, London, England

[21] Appl. No.: 629,647

[22] Filed: Jul. 11, 1984

[30] Foreign Application Priority Data

Jul. 13, 1983 [GB] United Kingdom ............... 8318889

[51] Int. Cl.$^4$ ................ C07C 121/52; C07C 161/02; C07D 257/04; A61K 31/41
[52] U.S. Cl. .................................. 514/381; 548/251; 548/252; 558/10; 558/405; 558/410
[58] Field of Search ............... 548/251, 252; 514/381; 558/10, 405, 410

[56] References Cited

U.S. PATENT DOCUMENTS 3,972,934 8/1976 Marshall ..................... 260/570.8 R

FOREIGN PATENT DOCUMENTS

| 28063 | 5/1981 | European Pat. Off. . |
| 54924 | 6/1982 | European Pat. Off. . |
| 56172 | 7/1982 | European Pat. Off. . |
| 0141234 | 12/1978 | Japan ................................. 558/390 |
| 2041363 | 9/1980 | United Kingdom . |

OTHER PUBLICATIONS

Chemical Abstracts 88:152148j (1978) Abstracting Oelschlaeger et al.
Mann et al., *J. Chem. Soc.*, 2819 (1954).
Buckle et al., *J. Med. Chem.*, 22(2), 158 (1979).

*Primary Examiner*—Glennon H. Hollrah
*Assistant Examiner*—D. B. Springer
*Attorney, Agent, or Firm*—Robert A. Conrad; Leroy Whitaker

[57] ABSTRACT

Compounds of formula $$R_2 \underset{R_1}{\diagdown} \diagup \underset{R_6}{\overset{R_3}{\diagdown}} \overset{R_5}{\underset{|}{-O-C-}} \diagdown \diagup R_7 - S_p - Z \quad (I)$$

wherein $R_1$, $R_2$ and $R_3$ are each independently selected from H, OH, $C_1$–$C_4$ alkyl, $R_4$—CO and halogen, where $R_4$ is $C_1$–$C_4$ alkyl; $R_5$ and $R_6$ are each independently selected from H, $C_1$–$C_4$ alkyl and optionally-substituted phenyl; $R_7$ is an alkylene group having from 1 to 4 carbon atoms, optionally containing a substituted or unsubstituted phenyl group; $p$ is 0 or 1; and Z is a 1H-tetrazol-5-yl or a —CN group; and salts thereof, may be prepared by reacting a compound of formula.

$$R_2 \underset{R_1}{\diagdown} \diagup \overset{R_3}{\diagdown} -OH$$

with a compound of formula $$Br-\overset{R_5}{\underset{\underset{R_6}{|}}{C}} \diagdown \diagup R_7-Br$$

wherein $R_1$–$R_7$ are as defined in claim 1, in an organic solvent at a temperature in the range of 40°–120° C. in the presence of a base, and reacting the resulting compound with an alkali metal cyanide or thiocyanate, and optionally reacting the resulting compound with a source of azide ions to produce pharmacologically active compounds of formula I wherein Z is 1H-tetrazol-5-yl.

17 Claims, No Drawings

TETRAZOLYL COMPOUNDS AND THEIR USE AS ANTI ALLERGIC AGENTS

This invention relates to compounds having pharmaceutical activity, to intermediates and processes for the preparation thereof.

The compounds of the invention have the formula

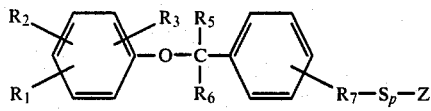

(I)

wherein $R_1$, $R_2$ and $R_3$ are each independently selected from H, OH, $C_1$-$C_4$alkyl, $R_4$—CO and halogen, where $R_4$ is $C_1$-$C_4$alkyl; $R_5$ and $R_6$ are each independently selected from H, $C_1$-$C_4$alkyl and optionally-substituted phenyl; $R_7$ is an alkylene group having from 1 to 4 carbons, optionally substituted with a phenyl or substituted phenyl group; p is 0 or 1; and Z is a 1H-tetrazol-5-yl or a —CN group; and salts thereof.

The compounds of formula (I) wherein Z is tetrazolyl are pharmacologically active and those wherein Z is —CN are intermediates employed in the preparation of the active compounds.

The term "$C_1$-$C_4$alkyl" refers to straight chain or branched hydrocarbons, and includes methyl, ethyl, propyl, isopropyl, butyl, iso-butyl and tertiary-butyl. The term "halogen" refers particularly to chlorine, bromine or fluorine. The term "optionally substituted phenyl" refers, for example, to unsubstituted phenyl or to phenyl with 1-3 substituents selected from OH, halogen, $NO_2$, $C_1$-$C_4$alkyl and $C_1$-$C_4$haloalkyl. The term "alkylene group having from 1 to 4 carbon atoms" includes straight and branched $C_1$-$C_4$ groups such as —$CH_2$—, ≦$CH(CH_3)$—, —$C(CH_3)_2$—, —$C(CH_3)(C_2H_5)$—, —$CH(C_3H_7)$—, —$CH_2$—$CH_2$—, —$CH(CH_3)$—$CH_2$—, —$CH(CH_3)$—$CH(CH_3)$—, —$CH(C_2H_5)$—$CH_2$—, —$(CH_2)_3$—, —$CH(CH_3)$—$CH_2$—$CH_2$— and —$CH_2$—$CH(CH_3)$—$CH_2$—. Alkylene groups substituted with a phenyl or substituted phenyl group refers to the above alkylene groups wherein one or more of the H atoms is replaced by a phenyl or substituted phenyl group as defined above.

A preferred group of compounds are those of formula

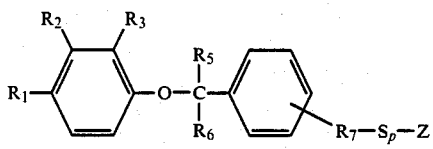

(II)

in which $R_7$ is —$(CH_2)_n$—, where n is 1 to 3 and $R_5$ and $R_6$ are both hydrogen. Most preferably $R_1$ is $CH_3$—CO, $R_2$ is OH and $R_3$ is propyl.

The preferred compounds of the invention are
1-{2-Hydroxy-3-propyl-4-[4-(1H-tetrazol-5-ylmethyl)-phenylmethoxy]phenyl}ethanone
1-{2-Hydroxy-3-propyl-4-{4-[3-(1H-tetrazol-5-yl)propyl]phenylmethoxy}phenyl}ethanone
1-{2-Hydroxy-3-propyl-4-[4-(1H-tetrazol-5-ylthiomethyl)phenylmethoxy]phenyl}ethanone
1-{2-Hydroxy-3-propyl-4-[3-(1H-tetrazol-5-ylthiomethyl)phenylmethoxy]phenyl}ethanone
1-{2-Hydroxy-3-propyl-4-{4-[2-(1H-tetrazol-5-ylthio)ethyl]phenylmethoxy}phenyl}ethanone
1-{2-Hydroxy-3-propyl-4-{4-[3-1H-tetrazol-5-ylthio)propyl]phenylmethoxy}phenyl}ethanone The most performed compounds are
1-{2-Hydroxy-3-propyl-4-}4-[3-(1H-tetrazol-5-yl)propyl]phenylmethoxy}phenyl}ethanone
1-{2-Hydroxy-3-propyl-4-{4-[2-(1H-tetrazol-5-ylthio)ethyl]phenylmethoxy}phenyl}ethanone The invention also provides a process for preparing a compound of formula (I) wherein Z is tetrazolyl which comprises reacting a compound of formula (I) wherein Z is CN with a source of azide ions preferably in the presence of a source of ammonium ions. Preferably the reaction is carried out using an alkali metal azide, such as sodium azide, in the presence of an ammonium halide, such as ammonium chloride. The reaction may be carried out in the presence of an inert solvent. When p is 1 the reaction is preferably carried out at a temperature of from 60°-90° C., in the presence of dioxan as solvent. When p is 0 the preferred reaction temperature is from 80° to 100° C., using DMF (dimethylformamide) as solvent.

Suitable salts of compounds of the invention include for example, those of mineral bases such as alkali metal hydroxides, especially the potassium or sodium salts, or alkaline earth metal hydroxides, especially the calcium salts, or of organic bases such as amines.

The preferred salts of the compounds of formula (I) wherein Z is tetrazolyl are those which are pharmaceutically-acceptable, but other derivatives are also included in the invention in as much as they are useful as intermediates in the preparation, purification or, characterization of the pharmaceutical end product.

The intermediate compounds of formula (I) wherein Z is CN may be prepared by reacting a compound of formula

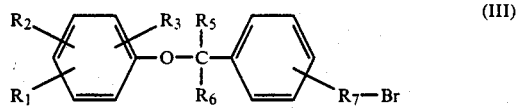

(III)

wherein $R_1$-$R_7$ and p are as defined above, with an alkali metal cyanide or thiocyanate in an organic solvent at a temperature of from 0° C. to 80° C. Preferably the reaction is carried out at room temperature using DMSO as a solvent.

The compounds of formula III may be prepared by reacting a compound of formula

with a compound of formula

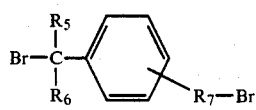

in an organic solvent at a temperature in the range of 40°-120° C. in the presence of a base. The preferred solvent is a ketone, such as methyl ethyl ketone (MEK) or methyl isobutyl ketone (MIBK).

The overall preferred process for producing compounds of formula (I) is indicated in the following reaction scheme.

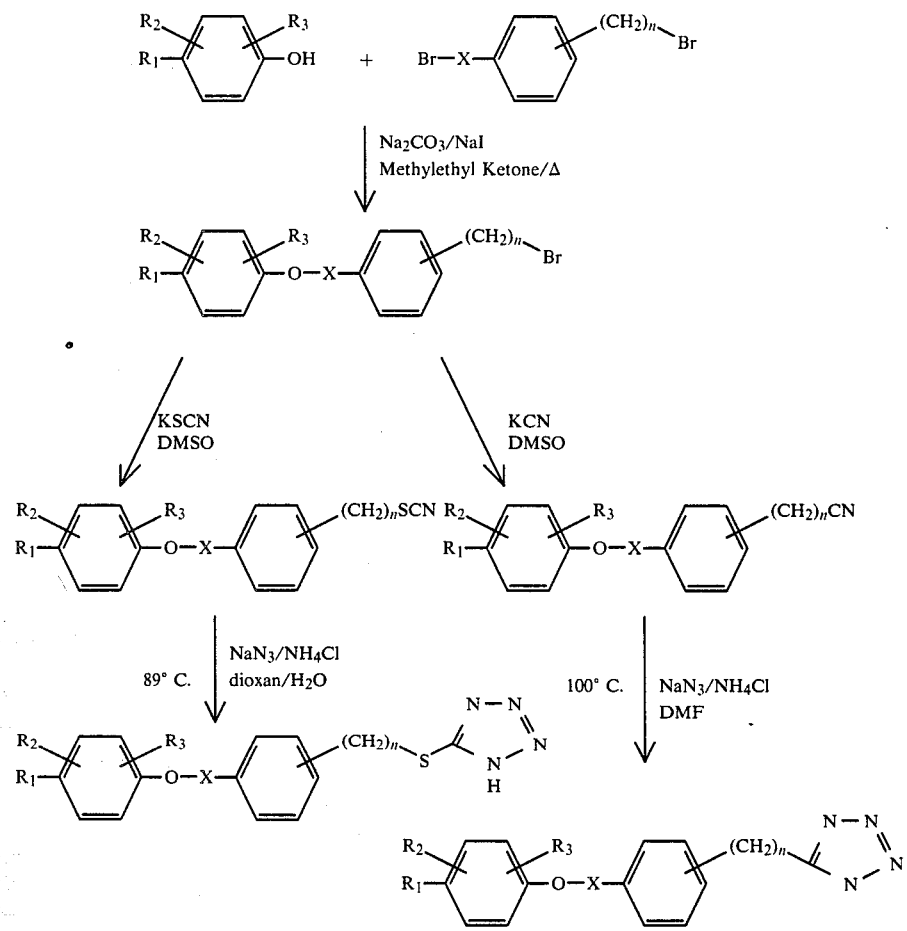

It will be appreciated that the compounds of formulae (I) may have one or more asymmetric carbon atoms. Thus if $R_5$ and $R_6$ are different groups their associated carbon atom will be optically active. Likewise $R_7$ may contain one or more optically active carbon atoms, thus giving rise to a number of possible enantiomers and diastereomers, mixtures of which can be separated by conventional methods.

The compounds of the present invention in which Z is tetrazolyl are pharmacologically active, being leukotriene antagonists as shown by the following tests; the in vitro test on guinea pig ileum segments at concentrations of from 10 ng to 50 μg, according to the method of Schild, 1947 Brit. J. Pharm. 2 197–206 (the pharmacological compounds of the following Examples exhibited an $IC_{50}$ against $LTD_4$ of less than $10^{-5}$ molar); the in vivo Guinea Pig Pulmonary Function Test of Austen and Drazen 1974 J. Clin. Invest. 53:1679–1685 at intravenous dosage levels of from 0.05 μg to 5.0 mg/kg; and a modified "Herxheimer" test at doses of from 25 to 200 mg/kg. The "Herxheimer" test is based on an allergic bronchospasm induced in guinea pigs and which closely resembles an asthmatic attack in man. The mediators causing the bronchospasm are very similar to those released when sensitised human lung tissue is challenged with an antigen. In the modified test employed in respect of compounds of the present invention, the animals were pretreated with a histamine antagonist, mepyramine, at a dose of 0.5 mg/kg i.p., 30 minutes before challenge. This modification masks the histamine effect to reveal better the leukotriene effect.

The compounds are accordingly indicated for therapeutic use in the treatment of diseases in which leukotrienes are implicated. These include allergic reactions of the pulmonary system in which leukotrienes are thought to be causal mediators of bronchospasm, for example, in allergic lung disorders such as extrinsic asthma and industrial asthmas such as Farmers lung and Pigeon Fanciers lung, and in other inflammatory disorders, for example, those associated with acute or chronic infectious diseases such as allergic skin diseases, ectopic and atopic eczemas, psoriasis, contact hypersensitivity and angioneurotic oedema, bronchitis, cystic fibrosis and rheumatic fever.

The compounds may be administered in free acid form, or in pharmaceutically acceptable salt form. They may be administered by various routes, for examples by the oral or rectal route, by inhalation, topically or parenterally, e.g. by injection, being usually employed in the form of a pharmaceutical composition. Such compositions form part of the present invention and are prepared in a manner well known in the pharmaceutical art and normally comprise at least one active compound in association with a pharmaceutically acceptable diluent or carrier. In making the compositions of the present invention, the active ingredient will usually be mixed with a carrier, or diluted by a carrier, and/or enclosed within a carrier which may, for example, be in the form of a capsule, sachet, paper or other container. Where the carrier serves as a diluent, it may be a solid, semi-solid, or liquid material which acts as a vehicle, excipient or medium for the active ingredient. Thus, the composition may be in the form of tablets, lozenges, sachets, cachets, elixirs, suspensions, aerosols (as a solid or in a liquid medium), ointments containing for example up to 10% by weight of the active compound, soft and hard gelatin capsules, suppositories, injection solutions and suspensions and sterile packaged powders. For administration by inhalation, particular forms of presentation include aerosols, atomisers and vaporisers.

Some examples of suitable carriers are lactose, dextrose, sucrose, sorbitol, mannitol, starches, gum acacia, calcium phosphate, alginates, tragacanth, gelatin, syrup, methyl cellulose, methyl- and propyl-hydroxybenzoate, talc, magnesium stearate and mineral oil. The compositions of the invention may, as is well known in the art, be formulated so as to provide quick, sustained or delayed release of the active ingredient after administration to the patient.

Where the compositions are formulated in unit dosage form, it is preferred that each unit dosage form contains from 10 mg to 1 g such as from 5 mg to 500 mg or from 25 mg to 200 mg. The term "unit dosage form" refers to physically discrete units suitable as unit dosages for human subjects and animals, each unit containing a predetermined quantity of active material calculated to produce the desired therapeutic effect, in association with the required pharmaceutical carrier.

The active compounds are effective over a wide dosage range and, for example, dosages per day will normally fall within the range of from 0.5 to 300 mg/kg, more usually in the range of from 5 to 100 mg/kg. However, it will be understood that the amount administered will be determined by the physician in the light of the relevant circumstances including the condition to be treated, the choice of compound to be administered and the chosen route of administration, and therefore the above dosage ranges are not intended to limit the scope of the invention in any way.

The following examples illustrate the invention.

EXAMPLE 1

1-[2-Hydroxy-3-propyl-4-(4-bromomethylphenylmethoxy)phenyl]ethanone

To a solution of 1-(2,4-dihydroxy-3-propyl phenyl) ethanone (10.0 g; 0.051 m) in dry methylethyl ketone (100 ml) was added dried anhydrous sodium carbonate (27 g; 5 mol. eq) and sodium iodide (0.5 g). To the stirred suspension was then added α,α'-dibromo-p-xylene (13.5 g; 0.051 m) and the suspension gently heated at reflux for five hours. The cooled suspension was evaporated under reduced pressure, the residue dissolved in water and extracted with dichloromethane (×2). The organic extract was washed with aqueous sodium hydroxide (2N), then water, dried over magnesium sulphate, filtered, and evaporated to dryness under reduced pressure to give a yellow solid. The solid was stirred with ether (200 ml) for 1 hour and filtered to remove any disubstituted impurity. The filtrate was evaporated under reduced pressure to leave a yellow solid. The solid was chromatographed on a U30 Sorbsil column using dichloromethane to give a white solid; recrystallised from ethanol, m.p. 98°–99° C.

EXAMPLE 2

1-{2-Hydroxy-3-propyl-4-[4-(2-bromoethyl)phenylmethoxy]phenyl}ethanone

To a solution of 1-(2,4-dihydroxy-3-propylphenyl)ethanone (10.0 g; 0.051 m) in dry methyl ethyl ketone (100 ml) was added dried anhydrous sodium carbonate (27 g; 5 mol eq) and sodium iodide (0.5 g). To the stirred suspension was added 4-(2-bromoethyl)phenylmethylbromide (14.2 g; 0.051 m) (literature preparation) and the suspension gently heated at reflux overnight. The cooled suspension was evaporated under reduced pressure, the residue taken up in water and extracted with dichloromethane (×2). The organic extract was washed with aqueous sodium hydroxide (2N), then water, dried over magnesium sulphate, filtered and evaporated under reduced pressure to give a yellow oil. The oil was chromatographed on a U30 Sorbsil column using dichloromethane to give a pale yellow oil which crystallised on standing to a white crystalline solid; recrystallised from ethanol m.p. 66°–70° C.

EXAMPLES 3–5

Similarly prepared were:
1-[2-Hydroxy-3-propyl-4-(2-bromomethylphenylmethoxy)phenyl]ethanone m.p. 137°–139° C. (EtOH)
1-[2-Hydroxy-3-propyl-4-(3-bromomethylphenylmethoxy)phenyl]ethanone m.p. 135°–136° C. (EtOH)
1-{2-Hydroxy-3-propyl-4-[4-(3-bromopropyl)phenylmethoxy]-phenyl}ethanone m.p. 66°–68° C. (EtOH)

EXAMPLE 6

1-[2-Hydroxy-3-propyl-4-(4-cyanomethylphenylmethoxy)phenyl]ethanone

1-[2-Hydroxy-3-propyl-4-(4-bromomethylphenylmethoxy)phenyl]ethanone (7.2 g; 0.02 m) and potassium cyanide (2.5 g; 0.04 m) where dissolved in dry dimethylsulphoxide (60 ml) and stirred at room temperature for 2 hours. The solution was poured onto water with stirring and filtered to give a cream solid, which was dried at 60° C. under reduced pressure; Recrystallised from ethanol to give a pale cream crystalline solid m.p. 75°–76° C.

EXAMPLES 7–10

Similarly prepared were:
1-[2-Hydroxy-3-propyl-4-(3-cyanomethylphenylmethoxy)phenyl]ethanone m.p. 114°–116° C. (EtOH)
1-[2-Hydroxy-3-propyl-4-(2-cyanomethylphenylmethoxy)phenyl]ethanone m.p. 157°–159° C. (EtOH)
1-Δ2-Hydroxy-3-propyl-4-[4-(2-cyanoethyl)phenylmethoxy]-phenyl}ethanone m.p. 120°–123° C. (EtOH)
1-{2-Hydroxy-3-propyl-4-[4-(3-cyanopropyl)phenylmethoxy]-phenyl}ethanone m.p. 37°–38° C. (EtOH)

EXAMPLE 11

1-[2-Hydroxy-3-propyl-4-(4-thiocyanomethylphenylmethoxy)phenyl]ethanone

1-[2-Hydroxy-3-propyl-4-(4-bromomethylphenylmethoxy)phenyl]ethanone (6.4 g; 0.017 m) and potassium thiocyanate (3.3 g; 0.034 m) were dissolved in dry dimethylsulphoxide (60 ml) and stirred at room temperature for 4 hours. The solution was then poured onto water, stirred and filtered to give a white solid; dried at 60° C. under reduced pressure. Recrystallised from ethanol to give a white crystalline solid m.p. 110°–111° C.

EXAMPLES 12–15

Similarly prepared were:

1-[2-Hydroxy-3-propyl-4-(3-thiocyanomethylphenylmethoxy)phenyl]ethanone m.p. 87°–88° C. (EtOH).

1-[2-Hydroxy-3-propyl-4-(2-thiocyanomethylphenylmethoxy)phenyl]ethanone m.p. 118°–120° C. (EtOH)

1-{2-Hydroxy-3-propyl-4-[4-(2-thiocyanoethyl)phenylmethoxy]phenyl}ethanone m.p. 87°–89° C. (EtOH)

1-{2-Hydroxy-3-propyl-4-[4-(3-thiocyanopropyl)phenylmethoxy]phenyl}ethanone m.p. 53°–55° C. (EtOH)

EXAMPLE 16

1-{2-Hydroxy-3-propyl-4-(4-(1H-tetrazol-5-ylmethyl)phenylmethoxy)phenyl}ethanone 1-[2-Hydroxy-3-propyl-4-(4-cyanomethylphenylmethoxy)phenyl]ethanone (4.25 g; 0.013 m) was dissolved in dry dimethylformamide (70 ml) to which was added sodium azide (3.42 g; 0.052 m) and ammonium chloride (1.4 g; 0.026 m). The resulting suspension was heated at 100° C. for 20 hours with stirring under a capillary air condenser. The cooled suspension was poured onto water with stirring, acidified and filtered to give a pale brown solid. The solid was taken up in aqueous sodium hydroxide (2N), washed with chloroform and acidified with concentrated hydrochloric acid with cooling and stirring, filtered to give a pale brown solid. Recrystallised from methanol to give a fawn crystalline solid m.p. 184°–187° C.

EXAMPLES 17–20

Similarly prepared were:

1-{2-Hydroxy-3-propyl-4-[2-(1H-tetrazol-5-ylmethyl)phenylmethoxy]phenyl}ethanone m.p. 202°–204° C. (MeOH)

1-{2-Hydroxy-3-propyl-4-[3-(1H-tetrazol-5-ylmethyl)phenylmethoxy]phenyl}ethanone m.p. 170°–173° C. (MeOH)

1-{2-Hydroxy-3-propyl-4-{4-[2-(1H-tetrazol-5-yl)ethyl]-phenylmethoxy}phenyl}ethanone m.p. 202°–204° C. (MeOH)

1-{2-Hydroxy-3-propyl-4-{4-[3-(1H-tetrazol-5-yl)propyl]-phenylmethoxy}phenyl}ethanone m.p. 136°–138° C. (MeOH)

EXAMPLE 21

1-{2-Hydroxy-3-propyl-4-[4-(1H-tetrazol-5-ylthiomethyl)phenylmethoxy]phenyl}ethanone 1-[2-Hydroxy-3-propyl-4-(4-thiocyanomethylphenylmethoxy)phenyl]ethanone (6.0 g; 0.017 m) was dissolved in dioxan:water (80:20; 100 ml) to which was added sodium azide (4.4 g; 0.068 m) and ammonium chloride (1.8 g; 0.034 m). The resulting solution was heated at 89° C. for 18 hours, cooled and poured onto water. The resulting solution was acidified with concentrated hydrochloric acid, filtered and washed with water to leave a white solid. Recrystallised from methanol to give a cream crystalline solid m.p. 160°–161° C.

EXAMPLES 22–25

Similarly prepared were:

1-{2-Hydroxy-3-propyl-4-[2-(1H-tetrazol-5-ylthiomethyl)-phenylmethoxy]phenyl}ethanone m.p. 174°–176° C. (MeOH)

1-{2-Hydroxy-3-propyl-4-[3-(1H-tetrazol-5-ylthiomethyl)-phenylmethoxy]phenyl}ethanone m.p. 146°–148° C. (MeOH)

1-{2-Hydroxy-3-propyl-4-{4-[2-(1H-tetrazol-5-ylthio)ethyl]phenylmethoxy}phenyl}ethanone m.p. 165°–168° C. (MeOH)

1-{2-Hydroxy-3-propyl-4-{4-[3-(1H-tetrazol-5-ylthio)propyl]phenylmethoxy}phenyl}ethanone m.p. 119°–121° C. (MeOH)

EXAMPLE 26

Tablet

| Active ingredient | 100 mg |
| Microcrystalline cellulose | 200 mg |
| Polyvinylpyrrolidone | 30 mg |
| Sodium carboxymethyl starch | 30 mg |
| Magnesium stearate | 5 mg |

The active ingredient and the microcrystalline cellulose are blended together and massed with a solution of polyvinylpyrrolidone in water. The mass is extruded through a screen, dried and starch and magnesium stearate. The granules are compressed on a suitable tablet machine.

EXAMPLE 27

Capsule

| Active ingredient | 50 mg |
| Starch flowable | 200 mg |
| Silicone fluid | 1 mg |

A portion of the starch is blended with the silicone fluid. To this mixture is added the active ingredient and the remainder of the starch. After mixing, the powder is filling into hard gelatine capsules.

EXAMPLE 28

Aerosol

| Active ingredient | 10 mg |
| Ethanol | 50 mg |
| Dichlorodifluoromethane (Propellant 12) | 658 mg |
| Dichlorotetrafluoroethane (Propellant 114) | 282 mg |

The active ingredient is dissolved in the ethanol. The concentrate is filled into extruded aluminium cans for inhalation aerosols. The cans are degassed with propellant 12 and sealed with an appropriate metered dose valve. The volume of product expelled per actuation is 50 or 100 μl equivalent to 0.5–1 mg active ingredient.

We claim:

1. A compound of formula

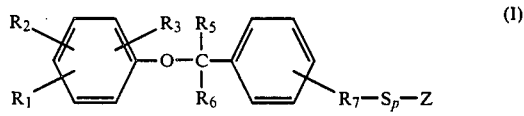

wherein $R_1$, $R_2$ and $R_3$ are each independently selected from H, OH, $C_1$–$C_4$alkyl, $R_4$—CO and halogen, where $R_4$ is $C_1$–$C_4$alkyl; $R_5$ and $R_6$ are each independently selected from H, $C_1$–$C_4$alkyl and optionally-substituted phenyl; R₇ is an alkylene group having from 1 to 4 carbon atoms, optionally containing a substituted or unsubstituted phenyl group; p is 0 or 1; and Z is a 1H-tetrazol-5-yl group; and pharmaceutically acceptable base addition salts thereof.

2. A compound of claim 1 wherein R₇ is —(CH₂)$_n$—, and n is 1, 2 or 3.

3. A compound of claim 2 wherein R₁ is CH₃—CO—.

4. A compound of of claim 3 wherein one of R₂ and R₃ is a 3-OH group and the other is methyl, ethyl or propyl in the 2-position.

5. A compound of claim 4 in which the substituted phenyl moiety attached to the O atom is 2-propyl-3-hydroxy-4-acetyl phen-1-yl.

6. A compound of claim 5 selected from the group consisting of
1-{2-Hydroxy-3-propyl-4-[4-(1H-tetrazol-5-ylmethyl)-phenylmethoxy]phenyl}ethanone
1-{2-Hydroxy-3-propyl-4-{4-[3-(1H-tetrazol-5-yl)propyl]phenylmethoxy}phenyl}ethanone
1-{2-Hydroxy-3-propyl-4-[4-(1H-tetrazol-5-ylthiomethyl)phenylmethoxy]phenyl}ethanone
1-{2-Hydroxy-3-propyl-4-[3-(1H-tetrazol-5-ylthiomethyl)phenylmethoxy]phenyl}ethanone
1-{2-Hydroxy-3-propyl-4-{4-(1H-tetrazol-5-ylthio)ethyl]phenylmethoxy}phenyl}ethanone and
1-{2-Hydroxy-3-propyl-4-{4-[3-(1H-tetrazol-5-ylthio)-propyl]-phenylmethoxy}phenyl}ethanone.

7. A pharmaceutical composition comprising a compound of claim 1 or a pharmaceutically acceptable base addition salt thereof in association with a pharmaceutically acceptable diluent or carrier.

8. A composition of claim 7 wherein in the compound of formula I R₇ is —(CH₂)$_n$— and n is 1, 2 or 3.

9. A composition of claim 8 wherein R₁ is CH₃—CO—.

10. A composition of claim 9 wherein one of R₂ and R₃ is a 3-OH group and the other is methyl, ethyl or propyl in the 2-position.

11. A composition of claim 10 in which the substituted phenyl moiety attached to the O atom is 2-propyl-3-hydroxy-4-acetylphen-1-yl.

12. A composition of claim 8 in which the compound of formula 1 is selected from the group consisting of
1-{2-Hydroxy-3-propyl-4-[4-(1H-tetrazol-5-ylmethyl)-phenylmethoxy]phenyl}ethanone
1-{2-Hydroxy-3-propyl-4-{4-[3-(1H-tetrazol-5-yl)propyl]phenylmethoxy}phenyl}ethanone
1-{2-Hydroxy-3-propyl-4-[4-(1H-tetrazol-5-ylthiomethyl)phenylmethoxy]phenyl}ethanone
1-{2-Hydroxy-3-propyl-4-[3-(1H-tetrazol-5-ylthiomethyl)phenylmethoxy]phenyl}ethanone
1-{2-Hydroxy-3-propyl-4-{4-[2-(1H-tetrazol-5-ylthio)ethyl]phenylmethoxy}phenyl}ethanone and
1-{2-Hydroxy-3-propyl-4-{4-[3-(1H-tetrazol-5-ylthio)propyl]phenylmethoxy}phenyl}ethanone.

13. A method of treating a mammal, including a human, suffering from an immediate hypersensitive disease, which comprises administering to the mammal an effective amount of a compound as defined in claim 1 or a pharmaceutically acceptable base addition salt thereof.

14. A compound of formula

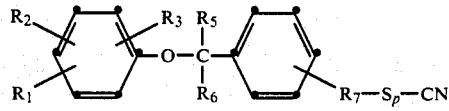

wherein R₁, R₂ and R₃ are each independently selected from H, OH, C₁–C₄alkyl, R₄-CO and halogen, where R₄ is C₁–C₄alkyl; R₅ and R₆ are each independently selected from H, C₁–C₄alkyl and optionally-substituted phenyl; R₇ is an alkylene group having from 1 to 4 carbon atoms, optionally containing a substituted or unsubstituted phenyl group; and p is 0 or 1.

15. A compound of claim 14 wherein R₇ is —(CH₂)$_n$—, and n is 1, 2 or 3.

16. A compound of claim 15 wherein R₁ is CH₃—CO—.

17. A compound of claim 16 in which the substituted phenyl moiety attached to the oxygen atom is 2-propyl-3-hydroxy-4-acetylphen-1-yl.

* * * * *